United States Patent [19]

Drake

[11] Patent Number: 4,629,533

[45] Date of Patent: Dec. 16, 1986

[54] ISOLATION OF 3-METHYL-1-BUTENE FROM A HYDROCARBON STREAM

[75] Inventor: Charles A. Drake, Bartlesville, Okla.

[73] Assignee: Phillips Petroleum Company, Bartlesville, Okla.

[21] Appl. No.: 697,091

[22] Filed: Jan. 31, 1985

[51] Int. Cl.$^4$ .............................................. B01D 3/40
[52] U.S. Cl. ........................................ 203/51; 203/58; 203/60; 203/91; 585/857; 585/865
[58] Field of Search .................... 203/51, 57, 91, 60, 203/58; 585/857, 860, 864, 865, 259, 273

[56] References Cited

U.S. PATENT DOCUMENTS

| | | | |
|---|---|---|---|
| 3,013,952 | 12/1961 | Clay | 202/39.5 |
| 3,075,025 | 1/1963 | Henke et al. | 260/681.5 |
| 3,155,597 | 11/1964 | Cornell et al. | 202/39.5 |
| 3,155,598 | 11/1964 | Cornell et al. | 202/39.5 |
| 3,158,555 | 11/1964 | Cornell | 202/39.5 |
| 3,206,377 | 9/1965 | Cornell et al. | 202/39.5 |
| 3,242,227 | 3/1966 | Kroeper et al. | 260/681.5 |
| 3,293,317 | 12/1966 | Whitney | 585/259 |
| 3,299,162 | 1/1967 | Clay | 260/680 |
| 3,317,627 | 5/1967 | King et al. | 585/864 |
| 3,320,138 | 5/1967 | Brandt et al. | 203/58 |
| 3,496,069 | 2/1970 | Tschoff et al. | 203/53 |
| 3,496,070 | 2/1970 | Woerner et al. | 203/62 |
| 3,634,537 | 1/1972 | Hutto | 208/321 |
| 3,755,488 | 8/1973 | Johnson et al. | 585/273 |
| 3,772,158 | 11/1973 | Sarno | 203/58 |
| 3,851,010 | 11/1974 | Rescalli et al. | 260/681.5 |
| 3,860,496 | 1/1975 | Ginnasi et al. | 203/28 |
| 3,890,208 | 6/1975 | Henneberg | 203/58 |
| 3,898,135 | 8/1975 | Tidwell et al. | 585/865 |
| 4,012,289 | 3/1977 | Haskell | 203/51 |
| 4,076,595 | 2/1978 | Haskell | 203/51 |
| 4,112,009 | 9/1978 | Rescalli et al. | 260/677 A |
| 4,134,795 | 1/1979 | Howat, III | 203/58 |
| 4,141,925 | 2/1979 | Paviov et al. | 260/681.5 C |
| 4,166,771 | 9/1979 | Haskell et al. | 203/58 |
| 4,310,388 | 1/1982 | Volkamer et al. | 585/864 |

FOREIGN PATENT DOCUMENTS 0023370  2/1981  European Pat. Off. ............ 585/865

*Primary Examiner*—S. Leon Bashore
*Assistant Examiner*—V. Manoharan
*Attorney, Agent, or Firm*—Mark A. Montgomery

[57] ABSTRACT

A process for recovering 3-methyl-1-butene from a hydrocarbon stream by treating the stream with a dimethylformamide/sulfolane solvent mixture to remove compounds which form azeotropes with 3-methyl-1-butene and separating the remaining stream.

8 Claims, No Drawings

ISOLATION OF 3-METHYL-1-BUTENE FROM A HYDROCARBON STREAM

BACKGROUND OF THE INVENTION

This invention relates to the treatment of hydrocarbon containing streams. It also relates to the treatment of amylene streams. In particular it relates to the recovery of 3-methyl-1-butene from a hydrocarbon stream. It further relates to the use of dimethyl formamide and sulfolane to treat the amylene stream so that 3-methyl-1-butene can be recovered in a distillation process.

Isolation of 3-methyl-1-butene from certain hydrocarbon streams has become an economically attractive route to recover 3-methyl-1-butene. However, distillation techniques are not successful for this separation because of an azeotrope formed by 3-methyl-1-butene and another stream component, 2-butyne.

The object of this invention is to recover 3-methyl-1-butene from a hydrocarbon stream.

SUMMARY OF THE INVENTION

According to the instant invention a dimethylformamide/sulfolane mixture is used in an extractive distillation to remove compounds which form azeotropes with 3-methyl-1-butene, such as 2-butyne, from a hydrocarbon stream to allow the recovery of 3-methyl-1-butene through conventional separation methods, such as distillation.

DETAILED DESCRIPTION OF THE INVENTION

According to the instant invention any hydrocarbon containing stream containing 3-methyl-1-butene and compounds which form azeotropes with 3-methyl-1-butene, can be used. Typical streams include the $C_5$- cut of a heavy gas oil catalytic cracking stream. An example of such a stream is a Goodyear amylene stream.

This invention particularly depends on mixtures of dimethylformamide and sulfolane, as dimethylformamide (DMF) or sulfolane used alone are not effective.

Generally the solvent mixture can run from about 30 weight percent DMF to about 70 weight percent DMF, with sulfolane comprising the remaining solvent. Preferably, the mixture will be about 50:50 DMF/to sulfolane.

The extractive distillation can be carried out in any range of temperature from about 100° C. to about 300° C. Preferably the temperature will be around 200° C.

The solvent mixture can be used in any amount. Generally, it can be used in an amount ranging from about 0.1 to about 20 times the weight of the hydrocarbon stream. Preferably, the amount of solvent mixture will range from about 0.5 to about 3.0. The solvent mixture and the hydrocarbon stream can be contacted from about 0.1 to about 30 minutes. Preferably they are contacted from about 0.5 to about 10 minutes.

The extractive process can be carried out using any conventional method for contacting fluids. This invention is not limited by the method employed in contacting the solvent mixture and the hydrocarbon containing stream. For example, the stream and the solvent mixture can be contacted in a liquid-liquid extraction process.

3-Methyl-1-butene is recovered from the insoluble organic material through conventional separation techniques, such as distillation, extraction, etc. The soluble component contains the solvent mixture, acetylenes and dienes, and particularly those compounds that form azeotropes with 3-methyl-1-butene, such as 2-butyne. This component is further treated to recover the solvent mixture.

The solvent mixture is recovered by diluting the solvent mixture layer with sufficient water to cause a separation of the solvent from the previously solubilized hydrocarbons. Once this separation occurs, the solvent mixture can be removed in any conventional manner and reconstituted to the desired concentration for recycle.

3-Methyl-1-butene is recovered using conventional separation techniques. A preferred method of recovering 3-methyl-1-butene is through distillation. The removal of those compounds which form azeotropes allows the recovery of the 3-methyl-1-butene.

The following examples demonstrate the advantages of this invention.

EXAMPLE I

A 220 g sample of "Goodyear amylene stream" was subjected to distillation at atmospheric pressure in a 60 tray Oldershaw distillation column at a reflux ratio of 60/1. Kettle temperature was maintained at 28°-36° C. throughout the distillation, with head temperature of 9°-26° C. for the samples collected. The compositions of several distillation cuts collected are given in Table I.

TABLE I

| Distillation of Amylene Stream at Atmospheric Pressure | | | | | | | | | |
|---|---|---|---|---|---|---|---|---|---|
| | Initial | 1 | 2 | 3 | 4 | 5 | 6 | 7 | Kettle |
| Head Temperature, °C. | — | 9 | 13 | 17 | 20 | 21 | 22 | 24 | — |
| Total % Overhead | — | 1.6 | 3.4 | 7.1 | 11.8 | 16.1 | 20.8 | 24.4 | — |
| Composition, % | | | | | | | | | |
| Butene | 24.1 | 57.4 | 50.2 | 20.1 | 8.1 | 1.9 | 0.4 | 0.1 | — |
| Isopentene | 11.6 | 3.7 | 1.4 | 19.2 | 8.0 | 14.6 | 27.6 | 30.8 | 7.0 |
| 3-MB-1 | 12.3 | 22.4 | 30.9 | 34.2 | 63.7 | 59.5 | 28.3 | 12.4 | 0.5 |
| 1-Pentene | 27.6 | 14.0 | 14.0 | 7.9 | 7.0 | 2.6 | 2.5 | 5.1 | 49.1 |
| 1,4-Pentadiene | 13.7 | 1.5 | 1.4 | 19.8 | 8.1 | 14.8 | 31.3 | 41.1 | 25.1 |
| 2-MB-2 | — | 0.4 | 0.3 | — | — | — | — | — | 8.5 |
| Isoprene | 7.4 | 0.1 | — | 0.2 | 0.1 | 0.1 | 0.1 | 0.1 | 8.5 |
| 2-Butyne | 2.9 | 0.4 | 1.0 | 7.3 | 4.2 | 6.5 | 9.3 | 8.8 | 0.9 |

It is seen that a normal distillation procedure is unsuccessful in achieving the desired separation of the 3-MB-1 from those materials such as 2-butyne and isoprene which form azeotropic mixtures with 3-MB-1.

EXAMPLE II

Extractive distillation employing several different solvents was carried out utilizing a common extractive distillation apparatus such as shown in, A. Weissberger, *The Technique of Organic Chemistry*, Vol. IV, Second Ed., Interscience Publishers, N.Y., p. 470, FIG. 15.

Solvent was pumped into the top of the unheated column, and amylene feed stream introduced at the top of the heated column. The heated zone was maintained at 200° C. (sufficient to vaporize the amylene feed, but not hot enough to vaporize the solvent). Solvent and amylene feed rates as well as the composition of the 3 hour distillation sample are presented in Table II. Run number one is presented for comparison—note that it corresponds to sample #4 from Example I.

TABLE II

| | Extractive Distillations of Amylene Stream Mixture | | | | |
|---|---|---|---|---|---|
| | | Run # | | | |
| | | 1 | 2 | 3 | 4 | 5 |
| Solvent | Initial | None | DMF | Solfolane | Tetradecane | 50% DMF/50% Sulfolane |
| Extractive distillation | — | No | Yes | Yes | Yes | Yes |
| Feed rates, mL/min | | | | | | |
| solvent | — | — | 1.5 | 1.75 | 1.75 | 1.75 |
| amylene stream | — | — | 0.75 | 0.75 | 0.75 | 0.75 |
| Composition, % | | | | | | |
| Butane | 0.1 | — | 0.4 | 0.2 | 0.1 | 2.3 |
| Butenes | 24.1 | 8.1 | 25.3 | 23.1 | 24.9 | 20.0 |
| Isopentene | 11.6 | 8.0 | 12.1 | 11.8 | 12.1 | 21.7 |
| 3-MB-1 | 12.3 | 63.7 | 12.1 | 12.5 | 11.9 | 24.6 |
| 1-Pentene | 27.6 | 7.0 | 28.0 | 28.8 | 27.0 | 21.1 |
| 1,4-Pentadiene | 13.7 | 8.1 | 12.6 | 12.9 | 13.7 | 9.0 |
| 2-MB-2 | — | — | — | — | — | — |
| Isoprene | 7.4 | 0.1 | 5.8 | 6.4 | 6.8 | 0.1 |
| 2-Butyne | 2.9 | 4.2 | 1.9 | 2.0 | 2.8 | 0.05 |

The results presented in Table II demonstrate the utility of mixed DMF-Sulfolane as an extractive distillation solvent for the removal of acetylenic compounds such as 2-butyne from a mixed $C_5$ stream as the bottoms product. It is to be particularly noted that the mixture of DMF and sulfolane (Run 5) is more effective in the extractive distillation than either DMF (Run 2) or sulfolane (Run 3) alone.

EXAMPLE III

The product composition profile for amylene feed treated with 50% DMF-50% sulfolane is presented in Table III. Distillation was carried out as described above, with solvent flow rate of 1.75 mL/min, amylene feed rate of 0.75 mL/min and heated column temperature of 200° C.

TABLE III

| Product Composition of Amylene Stream Mixture Before and After Extractive Distillation Using 50% DMF - 50% Sulfolane | | | | | | |
|---|---|---|---|---|---|---|
| | | Sample | | | | |
| | Initial | 1 | 2 | 3 | 4 | 5 |
| Composition, % | | | | | | |
| Butane | 0.1 | 1.3 | 2.2 | 2.4 | 2.3 | 2.0 |
| Butenes | 24.1 | 20.9 | 19.7 | 18.0 | 20.0 | 18.1 |
| Isopentane | 11.6 | 13.5 | 22.3 | 25.5 | 21.7 | 19.3 |
| 3-MB-1 | 12.3 | 12.7 | 20.5 | 24.1 | 24.6 | 23.3 |
| 1-Pentene | 27.6 | 36.3 | 23.5 | 20.3 | 21.2 | 21.0 |
| 1,4-Pentadiene | 13.7 | 12.3 | 9.8 | 8.2 | 9.0 | 9.0 |
| 2-MB-2 | — | — | — | — | — | — |
| Isoprene | 7.4 | 0.8 | 0.5 | 0.1 | 0.1 | 0.1 |
| 2-Butyne | 2.9 | 1.3 | 0.3 | 0.1 | 0.05 | — |

These data demonstrate that the 3-butyne and isoprene can be reduced to very low levels by extractive distillation with DMF-sulfolane. The 3-MB-1 can now be obtained from the stream through usual concentration and separation techniques.

EXAMPLE IV

Hydrotreating of an amylene stream also serves to remove azeotrope from compounds such as 2-butyne and dienes. About 260 g of Goodyear amylene stream which had been hydrotreated to remove these compounds was subjected to distillation at atmospheric pressure in a 60 tray Oldershaw column at a reflux ratio of 60/1. Kettle temperature was maintained at 28°–33° C. throughout the distillation, with head temperature varying from 11°–26° C. for the samples collected. The

TABLE IV

| Distillation of Hydrotreated Amylene Stream | | | | | | | | |
|---|---|---|---|---|---|---|---|---|
| | Sample | | | | | | | |
| | 1 | 2 | 3 | 4 | 5 | 6 | 7 | Kettle |
| Head Temperature, °C. | 11 | 15 | 17 | 20 | 23 | 25 | 26 | — |
| Total % Overhead | 3.0 | 5.5 | 9.6 | 13.0 | 18.3 | 21.5 | 25.1 | — |
| Composition, % | | | | | | | | |
| Butenes | 58.3 | 42.1 | 11.1 | 3.5 | 1.6 | 2.8 | 4.9 | 27.0 |
| Isopentene | 3.6 | 2.5 | 3.6 | 8.0 | 22.5 | 50.8 | 55.6 | 8.2 |
| 3-MB-1 | 24.6 | 52.1 | 81.3 | 80.3 | 58.0 | 20.2 | 8.5 | 0.3 |
| 1-Pentene | 1.1 | 0.3 | 0.3 | 0.8 | 4.3 | 11.1 | 20.3 | 44.4 |
| 1,4-Pentadiene | 20.0 | 1.8 | 3.2 | 7.1 | 13.3 | 14.7 | 10.4 | 3.2 | compositions of the distillation cuts collected are given in Table IV.

This experiment demonstrates the improved separation and isolation of 3-MB-1 possible by distillation of an amylene stream from which acetylenic compounds have been removed.

I claim:

1. A process for recovering 3-methyl-1-butene from a hydrocarbon stream containing 3-methyl-1-butene and compounds which form azeotropes with 3-methyl-1-butene comprising: extractive distillation of said hydrocarbon stream with a solvent mixture comprising dimethylformamide and sulfolane said solvent mixture present in an amount ranging from about 0.1 to about 20 times the weight of said hydrocarbon stream, where said dimethylformamide in the dimethylformamide/Sulfolane solvent mixture is present in an amount ranging from about 30 weight percent to about 70 weight percent based on the weight of said mixture, thereby separating insolubles containing said 3-methyl-1-butene as the overhead product stream from the bottoms product containing soluble compounds, the compounds that form azeotropes with 3-methyl-1-butene and the solvent mixture and thereafter recovering said 3-methyl-1-butene from said insolubles.

2. A process according to claim 1 where said hydrocarbon stream contains amylenes.

3. A process according to claim 2 where said hydrocarbon stream is a $C_5$-cut from a heavy gas oil catalytic cracking stream.

4. A process according to claim 3 where said stream contains 2-butyne.

5. A process according to claim 1 where said contacting takes place at a temperature ranging from about 100° C. to about 300° C. for about 0.1 to about 30 minutes.

6. A process according to claim 1 where the solvent mixture is recovered, treated with water, separated from the soluble hydrocarbons, and reconstituted for reuse.

7. A process according to claim 1 where said 3-methyl-1-butene is recovered by distillation.

8. A process according to claim 1 where said dimethylformamide comprises about 50 weight percent of said solvent mixture.

* * * * *